United States Patent
Alken

(10) Patent No.: US 7,317,039 B2
(45) Date of Patent: Jan. 8, 2008

(54) DEUTERATED SUBSTITUTED DIHYDROFURANONES AND MEDICAMENTS CONTAINING THESE COMPOUNDS

(75) Inventor: Rudolf-Giesbert Alken, Zepernick (DE)

(73) Assignee: BDD Berolina Drug Development GmbH, Neuenhagen (DE)

( * ) Notice: Subject to any disclaimer, the term of this patent is extended or adjusted under 35 U.S.C. 154(b) by 0 days.

(21) Appl. No.: 10/498,709

(22) PCT Filed: Dec. 11, 2002

(86) PCT No.: PCT/DE02/04591

§ 371 (c)(1), (2), (4) Date: Apr. 27, 2005

(87) PCT Pub. No.: WO03/050101

PCT Pub. Date: Jun. 19, 2003

(65) Prior Publication Data

US 2005/0176814 A1    Aug. 11, 2005

(30) Foreign Application Priority Data

Dec. 12, 2001   (DE) .................... 101 62 120

(51) Int. Cl.
*A61K 31/34* (2006.01)
*C07D 307/46* (2006.01)
(52) U.S. Cl. ..................... 514/461; 549/323
(58) Field of Classification Search ............. 549/295, 549/323; 514/461
See application file for complete search history.

(56) References Cited

U.S. PATENT DOCUMENTS 5,474,995 A * 12/1995 Ducharme et al. .......... 514/241

* cited by examiner

*Primary Examiner*—Bernard Dentz
(74) *Attorney, Agent, or Firm*—Kriegsman & Kriegsman

(57) ABSTRACT

The invention concerns deuterated substituted dihydrofuranones and pharmaceuticals containing these compounds.

In addition, the invention concerns the use of deuterated substituted dihydrofuranones for the treatment of symptoms for the irritating states of degenerative joint disorders, of acute pain and primary dysmenorrhea.

In addition, the invention discloses pharmaceutical compositions, which contain deuterated substituted dihydrofuranones as well as their physiologically compatible salts, in addition to pharmaceutically compatible adjuvants and/or additives, for the treatment of symptoms for the irritating states of degenerative joint disorders, of acute pain and primary dysmenorrhea.

20 Claims, No Drawings

DEUTERATED SUBSTITUTED DIHYDROFURANONES AND MEDICAMENTS CONTAINING THESE COMPOUNDS

The invention concerns deuterated substituted dihydrofuranones and pharmaceuticals containing these compounds.

A known representative of substituted dihydrofuranones is Rofecoxib (EP 705,254, U.S. Pat. No. 5,474,995), which is utilized as a selective COX-2 inhibitor, among other things, for the treatment of symptoms for the irritating states of degenerative joint disorders, acute pain in adults and primary dysmenorrhea.

The object of the present invention is to prepare substituted dihydrofuranones which have improved pharmacokinetic and/or pharmacodynamic properties when compared to compounds already known.

It has now been found surprisingly that the deuterated substituted dihydrofuranones according to the invention have essentially better pharmacokinetic and/or pharmacodynamic properties than the undeuterated compounds.

According to the invention the object is thus solved by the preparation of deuterated substituted dihydrofuranones of the general formula I:

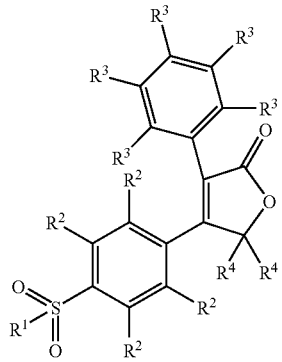

Formula I wherein $R^1$ is methyl or partially or completely deuterated methyl, $R^2$, independent of one another, indicates H or D, $R^3$, independent of one another, is H or D, $R^4$, independent of one another, indicates H or D, and wherein at least one of the groups $R^1$ to $R^4$ is D or contains D.

Deuterated substituted dihydrofuranones according to the general formula I are preferred, wherein $R^1$ is partially or completely deuterated methyl, $R^2$, independent of one another, indicates H or D, $R^3$, independent of one another, is H or D, and $R^4$, independent of one another, indicates H or D.

Deuterated substituted dihydrofuranones according to the general formula I are particularly preferred, wherein $R^1$ is methyl or partially or completely deuterated methyl, $R^2$ indicates D, $R^3$, independent of one another, is H or D, and $R^4$, independent of one another, indicates H or D.

Deuterated substituted dihydrofuranones according to the general formula I are especially preferred, wherein $R^1$ is methyl or partially or completely deuterated methyl, $R^2$, independent of one another, indicates H or D, $R^3$ is D and $R^4$, independent of one another, indicates H or D.

In addition, deuterated substituted dihydrofuranones according to the general formula I are preferred, wherein $R^1$ is methyl or partially or completely deuterated methyl, $R^2$, independent of one another, indicates H or D, $R^3$, independent of one another, is H or D, and $R^4$ indicates D.

Deuterated substituted dihydrofuranones according to the general formula I are advantageous, wherein $R^1$ is partially or completely deuterated methyl, $R^2$ indicates D, $R^3$, independent of one another, is H or D, and $R^4$, independent of one another, indicates H or D.

Deuterated substituted dihydrofuranones according to the general formula I are particularly advantageous, wherein $R^1$ is partially or completely deuterated methyl, $R^2$, independent of one another, indicates H or D, $R^3$ is D and $R^4$, independent of one another, indicates H or D.

Deuterated substituted dihydrofuranones according to the general formula I are especially advantageous, wherein $R^1$ is partially or completely deuterated methyl, $R^2$, independent of one another, indicates H or D, $R^3$, independent of one another, is H or D, and $R^4$ indicates D.

Deuterated substituted dihydrofuranones according to the general formula I are preferred according to the invention, wherein $R^1$ is methyl or partially or completely deuterated methyl, $R^2$ and $R^3$ are D and $R^4$, independent of one another, indicates H or D.

In addition, deuterated substituted dihydrofuranones according to the general formula I are preferred according to the invention, wherein $R^1$ is methyl or partially or completely deuterated methyl, $R^2$ indicates D, $R^3$, independent of one another, is H or D, and $R^4$ indicates D.

Deuterated substituted dihydrofuranones according to the general formula I are particularly preferred according to the invention, wherein $R^1$ is methyl or partially or completely deuterated methyl, $R^2$, independent of one another, indicates H or D, and $R^3$ and $R^4$ are D.

Deuterated substituted dihydrofuranones according to the general formula I are advantageous, wherein $R^1$ is partially or completely deuterated methyl, $R^2$ and $R^3$ are D and $R^4$, independent of one another, indicates H or D.

Deuterated substituted dihydrofuranones according to the general formula I are particularly advantageous, wherein $R^1$ is partially or completely deuterated methyl, $R^2$ indicates D, $R^3$, independent of one another, is H or D, and $R^4$ indicates D.

Deuterated substituted dihydrofuranones according to the general formula I are especially advantageous, wherein $R^1$ is partially or completely deuterated methyl, $R^2$, independent of one another, indicates H or D, and $R^3$ and $R^4$ are D.

Deuterated substituted dihydrofuranones according to the general formula I are preferred, wherein $R^1$ is methyl or partially or completely deuterated methyl, and $R^2$, $R^3$ and $R^4$ indicate D.

Deuterated substituted dihydrofuranones according to the general formula I are particularly preferred, wherein $R^1$ is partially or completely deuterated methyl, and $R^2$, $R^3$ and $R^4$ indicate D.

The following deuterated substituted dihydrofuranones are particularly preferred according to the invention:

d14-4-[4-(Methylsulfonyl)phenyl]-3-phenyl-2-(5H)-furanone,

4-[4-(Trideuteromethylsulfonyl)phenyl]-3-phenyl-2-(5H)-furanone,

4-[4-(Methylsulfonyl)-d4-phenyl]-3-phenyl-2-(5H)-furanone,

4-[4-(Methylsulfonyl)phenyl]-3-d5-phenyl-2-(5H)-furanone, 5,5-Dideutero-4-[4-(methylsulfonyl)phenyl]-3-phenyl-2-(5H)-furanone,
4-[d7-4-(Methylsulfonyl)phenyl]-3-phenyl-2-(5H)-furanone,
4-[4-(Trideuteromethylsulfonyl)phenyl]-3-d5-phenyl-2-(5H)-furanone,
5,5-Dideutero-4-[4-(trideuteromethylsulfonyl)phenyl]-3-phenyl-2-(5H)-furanone,
4-[4-(Methylsulfonyl)-d4-phenyl]-3-d5-phenyl-2-(5H)-furanone,
5,5-Dideutero-4-[4-(methylsulfonyl)-d4-phenyl]-3-phenyl-2-(5H)-furanone,
5,5-Dideutero-4-[4-(methylsulfonyl)phenyl]-3-d5-phenyl-2-(5H)-furanone,
4-[4-(Trideuteromethylsulfonyl)-d4-phenyl]-3-d5-phenyl-2-(5H)-furanone,
5,5-Dideutero-4-[4-(trideuteromethylsulfonyl)-d5-phenyl]-3-phenyl-2-(5H)-furanone,
5,5-Dideutero-4-[4-(trideuteromethylsulfonyl)phenyl]-3-d5-phenyl-2-(5H)-furanone,
5,5-Dideutero-4-[4-(methylsulfonyl)-d4-phenyl]-3-d5-phenyl-2-(5H)-furanone.

In addition, the use of the deuterated substituted dihydrofuranones according to the general formula I as well as their physiologically compatible salts is preferred for the treatment of symptoms for the irritating states of degenerative joint disorders, of acute pain and primary dysmenorrhea.

The use of the deuterated substituted dihydrofuranones according to the general formula I as well as their physiologically compatible salts is particularly preferred for producing pharmaceuticals for the treatment of symptoms for the irritating states of degenerative joint disorders, of acute pain and primary dysmenorrhea.

Pharmaceutical compositions are especially preferred, which contain deuterated substituted dihydrofuranones according to the general formula I as well as their physiologically compatible salts, in addition to pharmaceutically compatible adjuvants and/or additives, for the treatment of symptoms for the irritating states of degenerative joint disorders, of acute pain and primary dysmenorrhea.

The deuterated substituted dihydrofuranones according to the invention are produced in part according to known production processes for deuterated compounds as well as according to processes for producing undeuterated analogs, with the use of deuterated educts with a deuteration degree of over 98%.

Thus they are obtained by reaction of an optionally deuterated α-bromo-4-(methylsulfonyl)acetophenone, which can be obtained by bromination of optionally deuterated 4-(methylsulfonyl)acetophenone (analogous to U.S. Pat. No. 2,763,692 or EP 705,254), which is brought to reaction with optionally deuterated phenylacetic acid. The dihydrofuranones according to the invention are deuterated in positions $R^1$ and/or $R^2$ and/or $R^3$ and/or $R^4$, as a function of the educts used.

Various reaction paths are available for the synthesis of deuterated α-bromo-4-(methylsulfonyl)acetophenone. Thus according to Miura et al. (Bulletin of the Chemical Society of Japan, Vol. 50, No. 5, 1142-1146, 1977), starting with 2,3,4,5,6-d5-aniline, 2,3,4,5,6-d5-thiophenol can be produced, which is then S-methylated with methanol or deuterated methanol analogous to DE 2,649,590 or dimethyl sulfate or deuterated dimethyl sulfate analogous to EP 206,677. The deuterated methyl sulfide is then converted to deuterated 4-(methylthio)acetophenone by Friedel-Crafts acylation, for example, analogous to Cutler et al. (Journal of the American Chemical Society, Vol. 74, pp. 5475-5481, 1952), with the use of optionally deuterated acetyl chloride. Deuterated 4-(methylsulfonyl)acetophenone is obtained from this by oxidation, e.g., analogous to EP 705,254.

Another synthesis pathway for deuterated 4-(methylsulfonyl)acetophenone is conducted via deuterated 4-chloroacetophenone, which can be obtained by Friedel-Crafts acylation from deuterated chlorobenzene. This ethanone is reacted with optionally deuterated sodium methanethiolate, for example, analogously to JP 8143534, to form deuterated 4-(methylthio)acetophenone. The deuterated sodium methanethiolate can be obtained, analogous to DE 1,804,266, from deuterated methyl sulfide by reaction with NaOH.

The oxidation to the deuterated 4-(methylsulfonyl)-acetophenone can then be conducted as described in the first reaction path.

The deuterated phenylacetic acid used for the production of the deuterated dihydrofuranones according to the invention can be obtained commercially or is accessible analogous to known production processes for the undeuterated compound.

Common physiologically compatible inorganic and organic acids can be used for the production of physiologically compatible salts of the deuterated substituted dihydrofuranones according to the invention. These include, for example, hydrochloric acid, hydrobromic acid, phosphoric acid, sulfuric acid, oxalic acid, maleic acid, fumaric acid, lactic acid, tartaric acid, malic acid, citric acid, salicylic acid, adipic acid and benzoic acid. Other usable acids are, for example, described in Fortschritte der Arzneimittelforschung [Advances in Pharmaceutical Research], Vol. 10, pages 224-225, Birkhäuser Publishing Co., Basel and Stuttgart, 1966, and Journal of Pharmaceutical Sciences, Vol. 66, pages 1-5 (1977).

The acid addition salts are usually obtained in a way known in and of itself by mixing the free bases or their solutions with the corresponding acids or their solutions in an organic solvent, for example, a lower alcohol such as methanol, ethanol, n-propanol or isopropanol or a lower ketone such as acetone, methyl ethyl ketone or methyl isobutyl ketone or an ether such as diethyl ether, tetrahydrofuran or dioxane. For better crystal deposition, mixtures of the named solvents can also be used. In addition, physiologically compatible aqueous solutions of acid addition salts of the compounds used according to the invention can be prepared in an aqueous acid solution.

The acid addition salts of the compounds according to the invention can be converted into the free bases in a way known in and of itself, e.g., with alkalis or ion exchangers. Other salts can be obtained from the free bases, by reaction with inorganic or organic acids, in particular those which are suitable for the formation of therapeutically usable salts. These or even other salts of the new compound such as, e.g., the picrate, can serve also for the purification of the free base by converting the free base into a salt, separating the latter, and again releasing the base from the salt.

The subject of the present invention is also pharmaceuticals for oral, rectal, topical (percutaneous, transdermal, local), subcutaneoous, intravenous or intramuscular application, which contain, in addition to the usual vehicle and dilution agents, a compound of the general formula I or its acid addition salt as the active ingredient.

The pharmaceuticals of the invention are produced in the known way with the usual solid or liquid vehicle substances or dilution agents and the usually used pharmaceutical-technical adjuvants corresponding to the desired type of application with a suitable dosage. The preferred preparations exist in a form of administration which is suitable for oral application. Such administration forms include, for example, tablets, coated tablets, (sugar)-coated pills, capsules, pills, powders, solutions or suspensions or slow-release forms.

Topical application can be conducted, for example, in the form of salves, creams, gels, solutions, or by (adhesive) plasters.

Of course, parenteral preparations such as injection solutions are also considered. In addition, suppositories can also be named, for example, as preparations.

Corresponding tablets can be obtained, for example, by mixing the active ingredient with known adjuvants, for example, inert dilution agents such as dextrose, sugar, sorbitol, mannitol, polyvinylpyrrolidone, bursting agents such as corn starch or alginic acid, binding agents such as starch or gelatins, lubricants such as magnesium stearate or talcum and/or agents for obtaining a slow-release effect, such as carboxypolymethylene, carboxymethylcellulose, cellulose acetate-phthalate or polyvinyl acetate. The tablets can also comprise several layers.

Correspondingly, (sugar-)coated pills can be produced by coating cores, which are produced analogously to the tablets, with the agents usually employed in coating these pills, for example, polyvinylpyrrolidone or shellac, gum arabic, talcum, titanium dioxide or sugar. The envelope of the pill may also consist of several layers, whereby the above-mentioned adjuvants for tablets may be used.

Solutions or suspensions containing the active ingredient used according to the invention may additionally contain agents that improve taste such as saccharin, cyclamate or sugar, as well as, e.g., flavorings such as vanilla or orange extract. They may additionally contain suspension adjuvants such as sodium carboxymethylcellulose or preservatives such as p-hydroxybenzoate. Capsules containing active ingredients may be produced, for example, by mixing the active ingredient with an inert carrier such as milk sugar or sorbitol and encapsulating in gelatin capsules. Suitable suppositories can be prepared, for example, by mixing with support agents provided for this purpose, such as neutral fats or polyethylene glycol or derivatives thereof.

The production of the pharmaceuticals according to the invention for topical application is known to the person skilled in the art. In the production of the pharmaceuticals according to the invention for transdermal application, adjuvants and enhancer substances that are known in and of themselves are employed.

The production of the pharmaceutical preparations according to the invention is known in and of itself and is described in handbooks known to the person skilled in the art, for example: Hager's Handbuch (5th) 2, 622-1045; List et al., Arzneiformenlehre, Stuttgart: Scientific Publishing Co. 1985; Sucker et al., Pharmazeutische Technologie, Stuttgart: Thieme 1991; Ullmann's Enzyklopädie (5th) A 19, 241-271; Voigt, Pharmazeutische Technologie, Berlin: Ullstein Mosby 1995.

The compounds substituted with deuterium specifically aimed at according to the invention have a number of advantages when compared with the known compounds of the prior art, which contain deuterium only in the natural distribution. First of all, metabolism in the organism is slowed down due to the deuteration. Because of this, it is possible to change the dosage and to create preparations that are effective over a longer period of time, which can also improve compliance in the form of slow-release preparations.

In addition, the pharmacodynamics are also changed, since the deuterated compounds according to the invention form other hydrate envelopes, so that their distribution in the organism differs from the undeuterated compounds.

It is thus possible to develop novel forms of preparation. The following examples explain the invention:

EXAMPLE 1

Production of d10-4-(methylsulfonyl)acetophenone 88.1 g of the magnesium salt of monoperoxyphthalic acid are added to 20.9 g of d10-4-(methylthio)acetophenone in a mixture of 70 ml of methanol and 350 ml of dichloromethane while stirring, within 30 minutes. The reaction batch is stirred for 3 hours at room temperature, then filtered, and the filtrate is washed successively with 200 ml of aqueous, saturated sodium hydrogen carbonate solution and 100 ml of common salt solution. The aqueous phase is extracted with 200 ml of dichloromethane, the organic phases are combined and dried and the solvent is removed. One obtains 23.75 g of product as a white solid.

| Yield: 96% Melting point: 123-127° C. | | |
|---|---|---|
| Theoretical: | C: 51.89% | H: 9.67% |
| Experimental: | C: 51.99% | H: 9.72% |

$^{13}$C-NMR (200 MHz, CDCl$_3$): δ 23.00 (quint); 41.40 (quint); 125.90 (t); 129.80 (t); 142.00 (s); 142.60 (s); 196.20 (s).

EXAMPLE 2

Production of d9-α-bromo-4-(methylsulfonyl)acetophenone 36.57 g of d10-4-(methylsulfonyl)acetophenone are dissolved in 500 ml of chloroform and the solution is cooled to −5° C. 4 mg of aluminum chloride and 8 ml of bromine in 60 ml of chloroform are added successively. The reaction batch is mixed with 300 ml of water and the organic phase is separated. The aqueous phase is extracted with 200 ml of acetic acid ethyl ester, the organic phases are combined and dried. The solvent is removed and the crude product that remains is recrystallized from a mixture of acetic acid ethyl ester and hexane in a 1:1 ratio. One isolates 42.43 g of product as a white solid.

| Yield: 95% Melting point: 124-126° C. | | |
|---|---|---|
| Theoretical: | C: 37.77%; | H: 6.33% |
| Experimental: | C: 37.66%; | H: 6.20% |

13C-NMR (200 MHz, CDCl$_3$): (δ 41.40-41.90 (m); 125.90 (t); 129.80 (t); 142.00 (s); 142.60 (s); 196.20 (s).

EXAMPLE 3

Production of d14-4-[4-(methylsulfonyl)phenyl]-3-phenyl-2-(5H)-furanone 14.4 g of α,α,2,3,4,5,6-d7-phenylacetic acid are dissolved in 315 ml of acetonitrile containing 31 g of d9-α-bromo-4-

(methylsulfonyl)acetophenone at 25° C. and slowly mixed with 15.4 ml of triethylamine. The mixture is stirred for 20 minutes at room temperature and 30.05 ml of 1,8-diazabicyclo-[5.4.0]-undec-7-ene are added slowly, with ice cooling. The ice cooling is maintained and the reaction batch is stirred for 20 minutes. After acidifying with hydrochloric acid, 1200 ml of an ice/water mixture are added, and after several minutes, the precipitated crude product can be filtered off. The solid is washed with water and dissolved in 375 ml of chloroform. The solvent is dried and then 150 g of silica gel are added to it. The chloroform is removed insofar as this is possible and the product is then eluted from the silica gel with a 10% mixture of acetic acid ethyl ester/dichloromethane. 18.59 g of product are obtained from the solution as a light-yellow solid.

| Yield: 56% | | |
| --- | --- | --- |
| Melting point: 205-207° C. | | |
| Theoretical: | C: 62.17%; | H: 8.58% |
| Experimental: | C: 62.35%; | H: 8.67% |

$^{13}$C-NMR (200 MHz, CDCl$_3$): δ 41.40 (sept); 73.90 (quint); 125.50-125.90 (m); 127.20 (t); 127.90 (t); 128.70 (t); 135.20 (s); 138.00 (s); 139.50 (s); 144.80 (s); 165.00 (s).

The invention claimed is:

1. Deuterated substituted dihydrofuranones of the general formula I in concentrated form,

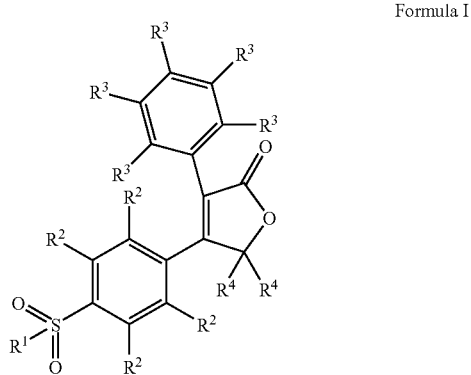

Formula I wherein
R$^1$ is methyl or partially or completely deuterated methyl,
R$^2$, independent of one another, indicates H or D,
R$^3$, independent of one another, is H or D,
R$^4$, independent of one another, indicates H or D, and wherein
at least one of the groups R$^1$ to R$^4$ is D or contains D.

2. Deuterated substituted dihydrofuranones according to claim 1, wherein
R$^1$ is partially or completely deuterated methyl,
R$^2$, independent of one another, indicates H or D,
R$^3$, independent of one another, is H or D, and
R$^4$, independent of one another, indicates H or D.

3. Deuterated substituted dihydrofuranones according to claim 1, wherein
R$^1$ is methyl or partially or completely deuterated methyl,
R$^2$ indicates D,
R$^3$, independent of one another, is H or D, and
R$^4$, independent of one another, indicates H or D.

4. Deuterated substituted dihydrofuranones according to claim 1, wherein
R$^1$ is methyl or partially or completely deuterated methyl,
R$^2$, independent of one another, indicates H or D,
R$^3$ is D and
R$^4$, independent of one another, indicates H or D.

5. Deuterated substituted dihydrofuranones according to claim 1, wherein
R$^1$ is methyl or partially or completely deuterated methyl,
R$^2$, independent of one another, indicates H or D,
R$^3$, independent of one another, is H or D, and
R$^4$ indicates D.

6. Deuterated substituted dihydrofuranones according to claim 1, wherein
R$^1$ is partially or completely deuterated methyl,
R$^2$ D,
R$^3$, independent of one another, is H or D, and
R$^4$, independent of one another, indicates H or D.

7. Deuterated substituted dihydrofuranones according to claim 1, wherein
R$^1$ is partially or completely deuterated methyl,
R$^2$, independent of one another, indicates H or D,
R$^3$ is D and
R$^4$, independent of one another, indicates H or D.

8. Deuterated substituted dihydrofuranones according to claim 1, wherein
R$^1$ is partially or completely deuterated methyl,
R$^2$, independent of one another, indicates H or D,
R$^3$, independent of one another, is H or D, and
R$^4$ D.

9. Deuterated substituted dihydrofuranones according to claim 1, wherein
R$^1$ is methyl or partially or completely deuterated methyl,
R$^2$ and R$^3$ are D and
R$^4$, independent of one another, indicates H or D.

10. Deuterated substituted dihydrofuranones according to claim 1, wherein
R$^1$ is methyl or partially or completely deuterated methyl,
R$^2$ indicates D,
R$^3$, independent of one another, is H or D, and
R$^4$ indicates D.

11. Deuterated substituted dihydrofuranones according to claim 1, wherein
R$^1$ is methyl or partially or completely deuterated methyl,
R$^2$, independent of one another, indicates H or D, and
R$^3$ R$^4$ are D.

12. Deuterated substituted dihydrofuranones according to claim 1, wherein
R$^1$ is partially or completely deuterated methyl,
R$^2$ and R$^3$ are D and
R$^4$, independent of one another, indicates H or D.

13. Deuterated substituted dihydrofuranones according to claim 1, wherein R$^1$ is partially or completely deuterated methyl, R$^2$ indicates D, R$^3$, independent of one another, is H or D, and R$^4$ indicates D.

14. Deuterated substituted dihydrofuranones according to claim 1, wherein R$^1$ is partially or completely deuterated methyl, R$^2$, independent of one another, indicates H or D, and R$^3$ and R$^4$ indicate D.

15. Deuterated substituted dihydrofuranones according to claim 1, wherein R$^1$ is methyl or partially or completely deuterated methyl, and R$^2$, R$^3$ and R$^4$ indicate D.

16. Deuterated substituted dihydrofuranones according to claim 1, wherein R$^1$ is partially or completely deuterated methyl, and R$^2$, R$^3$ and R$^4$ indicate D.

17. Deuterated substituted dihydrofuranones according to claim 1, selected from the group consisting of d14-4-[4-

(Methylsulfonyl)phenyl]-3-phenyl-2-(5H)-furanone; 4-[4-(Trideuteromethylsulfonyl)phenyl]-3 -phenyl-2-(5H)-furanone; 4-[4-(Methylsulfonyl)-d4-phenyl]-3-phenyl-2-(5H)-furanone; 4-[4-(Methylsulfonyl)phenyl]-3-d5-phenyl-2-(5H) furanone; 5,5-Dideutero-4-[4-(methylsulfonyl) phenyl]-3-phenyl-2-(5H)-furanone; 4-[d7-4-(Methylsulfonyl)phenyl]-3-phenyl-2-(5H)-furanone; 4-[4-(Trideuteromethylsulfonyl)phenyl]-3 -d5-phenyl-2-(5H)-furanone; 5,5-Dideutero-4-[4-(trideuteromethylsulfonyl) phenyl]-3-phenyl-2-(5H)-furanone; 4-[4-(Methylsulfonyl) -d4-phenyl]-3-d5-phenyl-2-(5H)-furanone; 5,5-Dideutero-4-[4-(methylsulfonyl) -d4-phenyl]-3-phenyl-2-(5H)-furanone; 5,5-Dideutero-4-[4-(methylsulfonyl)phenyl]-3-d5-phenyl-2-(5H)-furanone; 4-[4-(Trideuteromethylsulfonyl) -d4-phenyl]-3-d5-phenyl-2-(5H)-furanone; 5,5-Dideutero-4-[4-(trideuteromethylsulfonyl)-d5-phenyl]-3 -phenyl-2-(5H)-furanone; 5,5-Dideutero -4-[4-(trideuteromethylsulfonyl)phenyl]-3 -d5-phenyl-2-(5H)-furanone; and, 5,5-Dideutero-4-[4-(methylsulfonyl)-d4-phenyl]-3 -d5-phenyl-2-(5H)-furanone.

18. A method of treating symptoms for the irritating states of degenerative joint disorders, of acute pain and primary dysmenorrhea comprising administering to a patient suffering therefrom a therapeutically effective amount of a deuterated substituted dihydrofuranone according to claim 1 or a physiologically compatible salt.

19. A method for producing a pharmaceutical for the treatment of symptoms for the irritating states of degenerative joint disorders, of acute pain and primary dysmenorrhea comprising combining (i) a therapeutically effective amount of a deuterated substituted dihydrofuranone according to claim 1 or a physiologically compatible salt and (ii) a pharmaceutically compatible vehicle.

20. Pharmaceutical composition, which contains a therapeutically effective amount of a deuterated substituted dihydrofuranone according to claim 1 or a physiologically compatible salt, in addition to pharmaceutically compatible adjuvants and/or additives, for the treatment of symptoms for the irritating states of degenerative joint disorders, of acute pain and primary dysmenorrhea.

* * * * *